United States Patent [19]

Hunsucker

[11] 4,022,909
[45] May 10, 1977

[54] METHOD OF INHIBITING THE GROWTH OF BACTERIA USING QUATERNARY AMMONIUM COMPOUNDS

[75] Inventor: Jerry Hoyt Hunsucker, Terre Haute, Ind.

[73] Assignee: IMC Chemical Group, Inc., Terre Haute, Ind.

[22] Filed: July 6, 1976

[21] Appl. No.: 702,786

[52] U.S. Cl. .......................... 424/312; 252/51.5 A; 252/107; 260/29.6 MN
[51] Int. Cl.² .......................................... A01N 9/24
[58] Field of Search ..................................... 424/312

[56] References Cited

UNITED STATES PATENTS 3,272,712  9/1966  Kaldpissis et al. ............. 260/404 X
3,910,971  10/1975  Hunsucker ........................ 260/404

*Primary Examiner*—Allen J. Robinson
*Attorney, Agent, or Firm*—Roger A. Williams; Howard E. Post

[57] ABSTRACT

A method of inhibiting the growth of bacteria by contacting the bacteria and/or the environment inhabited by them with a compound represented by the general formula

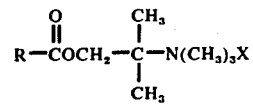

where R is an aliphatic hydrocarbon group of from 7 to 15 carbon atoms and X is a halogen atom.

9 Claims, No Drawings

METHOD OF INHIBITING THE GROWTH OF BACTERIA USING QUATERNARY AMMONIUM COMPOUNDS

BACKGROUND OF THE INVENTION

This invention relates to a method of inhibiting the growth of bacteria.

In a particular aspect, this invention relates to inhibiting the growth of bacteria on surfaces susceptible to bacterial growths.

More particularly, this invention relates to a method of preserving products that are susceptible to bacterial infestation, degradation, and decay.

SUMMARY OF THE INVENTION

It is an object of this invention to provide a method of inhibiting the growth of bacteria.

Another object of this invention is to provide a method of inhibiting the growth of bacteria on surfaces susceptible to such growth.

A further object is to provide a method of preserving products by inhibiting the growth of bacteria therein.

Still a further object of this invention is to provide a method of preserving products such as: recirculating cooling waters, cutting oils, drilling muds, starch adhesives, and latex paints.

Yet still a further object of this invention is to provide a method of disinfecting surfaces subject to bacterial growth.

Other objects of this invention will be apparent to those skilled in the art from the disclosure herein.

A method has been found for inhibiting the growth of bacteria when said bacteria or the environment inhabited by them are contacted with a compound or mixture thereof represented by the formula

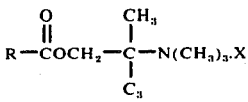

where R is an aliphatic hydrocarbon group of from 7 to 15 carbon atoms and X is a halogen atom.

DETAILED DISCUSSION

The compounds contemplated by the present invention include but are not limited to:
(2-Lauroyloxy-1,1-dimethylethyl)trimethylammonium iodide
(2-Myristoyloxy-1,1-dimethylethyl)trimethylammonium iodide
(2-Octanoyloxy-1,1-dimethylethyl)trimethylammonium iodide.

These compounds are readily prepared by methods known in the art, such as the method of Hunsucker U.S. Pat. No. 3,910,971, herein incorporated by reference, i.e. 2-dimethylamino-2-methyl-1-propanol (DMAMP) is esterified with a fatty acid represented by the formula RCOOH under esterification conditions. Suitable fatty acids include but are not limited to caprylic, lauric, myristic, palmitic, and stearic acids. Myristic acid is particularly preferred. These acids are all commercially available and the usual commercial grades are suitable for the practice of this invention. The commercial grade materials are not highly purified however and contain significant amounts of related fatty acids some of which are unsaturated. It is within the embodiment of this invention therefore that R in the formula can be provided by a mixture of saturated or unsaturated fatty acids from about 8 to about 18 carbon atoms.

The amino ester obtained as described above is treated with an alkyl halide to provide the quaternary ammonium halide salt of the amino-ester. A suitable alkyl halide is, e.g., a lower alkyl halide of from 1 to 4 carbon atoms, preferably a methyl halide. The halogen atom can be fluorine, chlorine, bromine or iodine. Preferred alkyl halides include methyl chloride and methyl iodide. The latter is particularly preferred.

The compounds useful in the practice of the invention described herein, exhibit a broad spectrum of antibacterial activity. The method may be employed to inhibit the growth of such bacteria. For example the method can be employed by adding a compound or mixtures of the compounds described by the above general formula to such environments as water, soil, and animate and inanimate matter whether animal or vegetable, living or dead. Those skilled in the antibacterial arts are aware of a great variety of ways in which the method of this invention can be advantageously employed.

The antibacterial method of this invention may be used to preserve or to disinfect substances which are subject to infestation with bacteria. The amount of compound added will depend on the product and the bacterial infestation and decay that it undergoes. A wide variety of products may be preserved by the method of this invention, such as pharmaceuticals, cosmetics, starch pastes, dispersion dyes, cutting and drilling oils, recirculating cooling waters, leather tanning solutions, water and oil base paints and the like.

The compounds employed in the method of this invention may generally be used as preservatives in any convenient, antibacterially-effective concentrations. Generally concentrations from about 0.001 to about 0.01% by weight thereof are effective. Amounts of at least 0.001% by weight are preferably used. Lesser amounts than 0.001% do not generally achieve significant antibacterial effectiveness. Amounts greater than about 0.01% are not generally necessary to achieve effective antibacterial activity. A particularly preferred range is from about 0.001 to about 0.005%.

A compound or a mixture of the compounds of the above described general formula are useful in preserving both oil-based and water-based paints of formulations well-known to those skilled in the art. When used as a preservative in both oil-based and water-based paints the compound or mixture of compounds is used in a quantity from about 0.001% to about 0.005% by weight. Similarly a cutting oil with the general formula of mineral oil, emulsifier, and water can be preserved against bacterial attack by adding thereto from about 0.001 to about 0.005% by weight, a compound used in the method of this invention. Still further, cosmetic preparations can be preserved against microbial infestation by adding to the preparations a compound of the above formula used in the method of this invention in an amount from about 0.001 to about 0.005% of the total weight of the preparation.

When the antibacterial compounds of the method of this invention are used as disinfectants, they may be applied to any surface or environment to protect such surface or environment from the growth of bacteria. Such surfaces and environments include the soil, water, walls, ceilings, floors, cloth, materials and the like. A compound of this method may be applied to such surfaces and environments directly, diluted, or in other dispersed form. A compound can be emulsified in water or diluted in any appropriate organic diluent such as lower alcohols, esters, ketones, chlorinated hydrocarbons, aliphatic and aromatic hydrocarbons, etc., and then applied to the surface or environment. The compounds are relatively insoluble in water but can be emulsified by any suitable method, many of which are known. For example the compounds of this invention can be emulsified with water and a suitable surfactant to make a water-emulsion containing from about 1 to 25 parts of the compound and from 75 to 99 parts water, then applied to or plowed into the soil in a manner such that the final concentration of the compound in the soil will be from about 10 to about 50 ppm. to inhibit the growth of bacteria therein. The compounds have a low order of toxicity in mammals. The compounds are especially suited as disinfectants for farm buildings and farm animals. The compounds are easily applied as sprays, dusts, or by brushing. Because of their low water solubility the compounds advantageously form an antibacterial film on surfaces to which they are applied. The compounds can further be dispersed in environments in dry form by combining the compounds used in the method of this invention with such dry dispersants as clay, talc, refined silicates, wood flour, sand, magnesium oxide, calcium carbonate, fuller's earth, kaolin, diatomaceous earth, mica, pumice and the like. For example an agricultural preparation can be prepared by mixing from about 1 to 25 parts of the compounds with from about 75 to 99 parts of one of the aforementioned dry dispersants. These preparations may be spread on such environments as the soil or intermixed therein, e.g. by plowing into the soil in a manner such that the final concentration of the compound will be from about 10 to about 50 ppm.

Further the compounds in the method of this invention may be applied to surfaces in combination with other preparations such as soaps, cleansers, paints and the like. Generally the compounds comprise from about 0.001 to about 0.005% of the preparation by weight. Generally lesser amounts than 0.001% do not achieve significant antibacterial effectiveness and amounts greater than 0.01% are not generally necessary to achieve effective antibacterial activity. These preparations impart a thin film on surfaces to which they are applied and this film contains the compounds in the proper concentration to inhibit the growth of bacteria thereon. For example a paint with the general paint formulation well-known in the art will impart antibacterial activity to the surface on which it is coated when from about 0.001 to about 0.005% by weight of a compound of the above-given formula is mixed therein. Similarly an antibacterial soap can be prepared by adding from about 0.001 to about 0.005% of a compound of the above-given formula to a mixture of 60% coconut fatty acid, 40% stearic fatty acid, dye, perfume, and extender. By adding any of the mixtures of the compounds of the above-given formula to these preparations the growth of bacteria on the surfaces to which these preparations are applied will be inhibited and any future growth of bacteria on the surfaces to which these preparations are applied will also be inhibited. Because of their low water solubility the compounds advantageously form an antibacterial film on surfaces to which they are applied. The invention will be better understood with reference to the following examples. It is understood that these examples are intended for illustration only and it is not intended that the invention be limited thereby.

EXAMPLE 1

DMAMP 125 g (1.07 mole) and commercial grade myristic acid 232 g (the acid had an equivalent weight of 232) were charged to an esterification vessel equipped with an agitator distillation column, decanter head, thermometer and heat source. Toluene sulfonic acid 2 g was added as a catalyst. The mixture was heated with agitation from about 160° to about 170° C until the acid number was less than 20. It was cooled and another 5 ml of DMAMP (about 5 g) was added and the mixture was again heated to 171° C for 2½ hours. The acid number was about 15. Toluene, about 40 ml, was added and stripped to remove any remaining water. The residue was washed with an equal volume of 50 percent sodium hydroxide solution. Petroleum ether, 350 ml, was added and the mixture was separated. The petroleum ether was separated by evaporation and distillation at 1 mm. The product cut distilled at 150°–156°. It had a neutral equivalent of 340.3 compared with a theoretical value of 330.1. It was concluded that the product was the myristic acid ester of DMAMP (2-dimethylamino-2-methyl-1-propyl myristate).

A 32.75 g portion of the ester, prepared as described above, and 14.20 g of methyl iodide were mixed with 50 g of chloroform in a reaction vessel equipped with a reflux condenser. The mixture was heated for 60 minutes at reflux and was then cooled. It was mixed with an equal volume of diethyl ether and chilled in a freezer at -10° C. The crystals that separated were filtered and washed with cold ether. There was obtained (2-myristoyloxy-1,1-dimethylethyl)-trimethylammonium iodide, m.p. 168.4° having a nitrogen content of 3.42 percent and iodine 25.89 percent.

The product had an $LD_0$ of 600 mg/kg by oral administration to mice, and $LD_{50}$ of 1000 mg/kg and an $LD_{100}$ of 2000 mg/kg.

The compound was tested for antibacterial and antifungal activity by the streak plate test, which is known in the art. The test substance was incorporated into several portions of an agar medium at several known concentrations and the mixtures were placed in Petri dishes. Then streaks of test organisms were applied to the surface of the medium, the dishes were incubated under growth-promoting conditions, and then examined for growth of organisms. The results are reported as the Inhibition End-Point Range, the lower figure signifying a concentration that allows growth and the higher figure being a concentration that inhibits growth. The ranges for a variety of organisms are given in the table. It was concluded that the compound exhibited powerful antibacterial activity.

The compound is employed as a spray disinfecting buildings and pens used for houseing animals. An emulsion is prepared by dissolving about 10 g of the product prepared as described above in 100 ml of kerosene adding 2 g of emulsifying agent and adding gradually to 1 liter of water at 80° C with agitation. The resulting emulsion is used for spraying.

EXAMPLE 2

The lauric acid ester of DMAMP was prepared by mixing 200 g of commercial grade lauric acid with 125 g of DMAMP and 2 g of toluene sulfonic acid in a reaction vessel equipped with an agitator, heat source, thermometer, distillation column and decanter head. Toluene was added to assist in removal of water as the azeotrope. The mixture was heated at about 115°–120° C until the acid member was 28 and 22 ml of water had been removed. The product was purified by distilling through a Vigreaux distillation column at a liquid temperature of about 150°–160° C and a pressure of 1 mm. The fraction distilling at 152°–157° was taken as the product. It had a neutral equivalent of 354 and an acid number of 35.5.

A 29.9 g (0.1 mole) portion of the ester obtained above was mixed with chloroform 50 ml in a 500 ml flask equipped with an agitator, thermometer and reflux condenser. Methyl iodide 15 g was added slowly with agitation then heated at reflux for about an hour at about 65° C. The product was then cooled and an equal amount of anhydrous ether was added resulting in a heavy precipitate. After chilling at 0°–5° the mixture was filtered and the solids were then recrystallized from acetone, slurried with ether and filtered. There was obtained (2-lauroyloxy-1,1-dimethyl)-trimethylammonium iodide, m.p. 164° C, N 3.15 percent compared with theoretical 3.08 percent.

The compound was tested for oral toxicity by oral administration to mice. It had an $LD_0$ of 500 mg/kg, $LD_{50}$ of 900 mg/kg and $LD_{100}$ of 1700 mg/kg. When tested by the streak plate method it exhibited strong antibacterial activity against a variety of bacteria, as shown in the table, but only slight activity against fungi.

EXAMPLE 3

The experiment of Example 2 was repeated in all essential details except that commercial grade palmitic acid 256 g was substituted for lauric acid and the mixture was heated at about 179°–190° C. There was obtained 2-dimethyl-amino-2-methyl-1-propyl palmitate having an acid number of 23.4.

A 36 g portion of the ester obtained above was reacted with methyl iodide 15 g as described in Example 2. There was obtained (2-palmitoyloxy-1,1-dimethylethyl)-trimethylammonium iodide, m.p. 170.8° C.

It was tested for acute oral toxicity in mice. The $LD_0$ was 800 mg/kg; and $LD_{50}$ was 1490 mg/kg; and the $LD_{100}$ was 3200 mg/kg.

The product was tested for antibacterial activity by the streak plate test. The results are shown in the table. The compound was only slightly active against fungi.

The product is employed as a disinfectant by forming an emulsion in the manner described in Example 1 to provide concentration of above about 50 μg/ml to control the growth of bacteria when applied to a hard surface.

EXAMPLE 4

DMAMP 118 g (1 mole) and commercial grade caprylic acid 131 g (1 mole) were dissolved in 35 ml of toluene. The mixture was heated under reflux at about 140°–165° until 20 ml distillate was recovered and no more was being collected. The pressure was then reduced to 10mm and distillation was continued to about 130° C to strip off toluene and water. The pressure was then reduced to about 1 mm and the main product fraction was recovered at a liquid temperature of about 106°–109°. There was obtained 2-dimethylamino-2-methyl-propyl caprylate, neutral equivalent 247.9 compared with theoretical 244.

A portion of the product obtained above was reacted with methyl iodide as described in Example 2. There was obtained (2-octanoyloxy-1,1-dimethylethyl)trimethylammonium iodide, m.p. 135.8°. The nitrogen content was 3.98 percent compared with theoretical 3.77 and the iodine content was 32.91 percent compared with theoretical 34.23 percent.

The product was tested for acute oral toxicity in mice. The $LD_0$ was 800 mg/kg; the $LD_{50}$ was 1160 mg/kg; and $LD_{100}$ was 1700 mg/kg.

The product was tested for antibacterial activity by the streak plate test. The results are given in the table.

The product is used as a disinfectant at a concentration of greater than about 1000 μg/ml to control the growth of bacteria.

TABLE

| Organism | Gram Designation | Inhibition Endpoint in μg/ml | | | |
|---|---|---|---|---|---|
| | | Example 1 | Example 2 | Example 3 | Example 4 |
| Staphylococcus aureus | + | 1–5 | 1–5 | 1–5 | 100–500 |
| Streptococcus fecalis | + | 1–5 | 5–10 | 1–5 | >1000 |
| Streptococcus hemolyticus | + | 1–5 | 5–10 | 1–5 | >1000 |
| Escherichia coli | − | 100–500 | 100–500 | >1000 | 500–1000 |
| Pasteurella pseudotuberculosis | − | 1–5 | 5–10 | 100–500 | 100–500 |
| Pseudomonas auriginosa | − | >1000 | 500–1000 | >1000 | >1000 |
| Shigella dysenteriae | − | 5–10 | 10–50 | 50–100 | >1000 |
| Gaffkya tetragena | + | 1–5 | — | — | — |
| Micrococcus flavus | + | 0.1–0.5 | — | — | — |
| Mycobacterium ranae | Acid fast | 1–5 | 1–50 | 50–100 | 100–500 |

The method of this invention is employed to inhibit the growth of bacteria. A compound or a mixture of compounds utilized in the method of this invention are placed in contact with the environment as part of preparations applied to the environment. Such preparations include water emulsions, powders, paints, soaps, cleansers, and the like such as illustrated by but not limited to the following examples.

EXAMPLE 5

A water-based solution was prepared by the following general formula.

| Solution A | |
|---|---|
| (2-Lauroyloxy-1,1-dimethyl)-trimethylammonium iodide | 10 g |
| Ethylene Glycol | 10 g |

The 2-lauroyloxy-1,1-dimethyl)-trimethylammonium iodide was dissolved in the ethylene glycol by heating to 50°–60° C. This solution was used as follows:

| Solution A | 2 g |
|---|---|
| Water | 6 g |

-continued

| | |
|---|---|
| Denatured Ethanol | 2 g |

The above were mixed at room temperature to produce a water solution. The solution is sprayed onto a plot of soil and the growth of bacteria therein is inhibited.

EXAMPLE 6

An agricultural preparation is prepared by the following general formula.

| Agricultural Preparation | Parts |
|---|---|
| (2-Myristoyloxy-1,1-dimethyl-ethyl)-trimethylammonium iodide | 15 |
| Clay (inert diluent) | 85 |

The ingredients are comminuted and thoroughly mixed. The agricultural preparation is spread on a plot of soil and plowed therein in such a manner that the final concentration of (2-myristoyloxy-1,1-dimethylethyl)-trimethylammonium iodide is at least 10 ppm. The growth of bacteria therein is inhibited.

EXAMPLE 7

An oil-based paint is prepared according to the following general formula

| Paint | Parts |
|---|---|
| Titanium dioxide | 17.5 |
| Zinc oxide | 14.1 |
| Calcium carbonate | 28.2 |
| 325 Mesh Water ground Mica | 3.07 |
| Alkali refined linseed oil | 21.1 |
| X-bodied linseed oil | 7.55 |
| 24% lead naphthenate | .70 |
| 6% manganese naphthenate | .105 |
| (2-Octanoyloxy-1,1-dimethyl)-trimethylammonium iodide | .005 |
| Mineral spirits to bring the viscosity to 82 KU (Krebs Units) | 7.46+ |

The paint in applied to a wall and bacterial growth on the wall is inhibited.

EXAMPLE 8

An antimicrobial soap is prepared by the following formula

| Antimicrobial Soap | Parts |
|---|---|
| Coconut fatty acid | 56 |
| Stearic fatty acid | 35 |
| Dye | 1 |
| Perfume | 1 |
| Extender | 7 |
| (2-Lauroyloxy-1,1-dimethyl-ethyl)-trimethylammonium iodide | 0.005 |

The soap is used as a disinfectant to wash tile surfaces. A thin film is coated on the surface and bacterial growth thereon is inhibited.

EXAMPLE 9

An antiseptic cleansing agent for laundries is prepared by the following formula.

| Antiseptic Cleansing Agent for Laundries | Parts |
|---|---|
| Sodium coconut fatty alcohol sulfate | 22.0 |
| Sodium tripolyphosphate | 33.0 |
| Sodium carbonate | 9.0 |
| Sodium sulfate | 13.0 |
| Water glass | 5.0 |
| Sodium carboxymethyl-cellulose | 0.005 |
| (2-Myristoyloxy-1,1-dimethyl-ethyl)-trimethylammonium iodide | 7.0 |
| Water | 11.0 |

The cleansing agent is used to wash clothes. It leaves a thin film on which the growth of bacteria is inhibited.

In addition to being utilized for obtaining antibacterial efficacy, the method of this invention may also be used in accordance with the invention for preserving consumer-type products such as cosmetics, starch pastes, dispersion dyes, cutting and drilling oils, paints, pharmaceuticals, and the like which are subject to bacterial degradation and infection. Examples of the preservative use of this method are given below.

EXAMPLE 10

A daycream and lotion of the following formula is preserved against bacterial growth. It contains 0.005 parts (2-lauroyloxy-1,1-dimethylethyl)-trimethylammonium iodide.

| Daycream and Lotion | Parts |
|---|---|
| Decyl oleate | 10.0 |
| Vegetable oill | 10.0 |
| Glycerine 28° Be | 5.0 |
| Colloidal suspension mixture of 90 parts C$_{16}$ to C$_{18}$ alcohol and 10 parts sodium lauryl sulfate | 16.0 |
| (2-Lauroyloxy-1,1-dimethylethyl)-trimethylammonium iodide | 0.005 |
| Water | 59.0 |

EXAMPLE 11

A cutting oil prepared according to the following formula is protected against bacterial growth therein.

| Cutting Oil | Parts |
|---|---|
| Mineral oil | 30 |
| Emulsifier, mahogany sulfonate | 6 |
| (2-Myristoyloxy-1,1-dimethylethyl)-trimethylammonium iodide | 0.005 |
| Water | 64 |

EXAMPLE 12

A paint prepared in accordance with the following formula is protected against bacterial growth therein.

| Paint | Parts |
|---|---|
| Basic carbonate white lead | 16.0 |
| Basic sulfate white lead | 16.0 |
| Zinc oxide | 13.2 |
| Titanium-Barium | 13.2 |
| Magnesium silicate | 6.6 |
| Linseed oil | 26.5 |
| Tung oil | 4.1 |
| Drier | 1.7 |
| (2-Octanoyloxy-1,1-dimethyl-ethyl)-trimethylammonium iodide | 0.005 |
| Turpentine | 1.4 |
| Petroleum spirits | 1.3 |

I claim:

1. A method of inhibiting the growth of bacteria comprising contacting the bacteria or the environment inhabited by them with a growth inhibiting amount of a compound or mixture thereof represented by the formula:

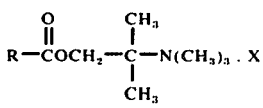

where R is an aliphatic hydrocarbon group of from 7 to 15 carbon atoms and X is a halogen atom.

2. The method of claim 1 wherein R is an aliphatic group of 7 carbon atoms.

3. The method of claim 1 wherein R is an aliphatic group of 11 carbon atoms.

4. The method of claim 1 wherein R is an aliphatic group of 13 carbon atoms.

5. The method of claim 1 wherein R is an aliphatic group of 15 carbon atoms.

6. The method of claim 1 wherein R is provided by a mixture of saturated and unsaturated fatty acids, the acids having from 8 to 16 carbon atoms.

7. The method of claim 1 wherein X is iodine.

8. The method of claim 1 wherein X is chlorine.

9. The method of claim 1 wherein said bacteria are contacted by applying to the bacteria or the environment inhabited by them a water emulsion containing said compound.

* * * * *

UNITED STATES PATENT AND TRADEMARK OFFICE
CERTIFICATE OF CORRECTION

PATENT NO. : 4,022,909
DATED : May 10, 1977
INVENTOR(S) : Jerry H. Hunsucker

It is certified that error appears in the above-identified patent and that said Letters Patent are hereby corrected as shown below:

Column 1, line 40, in the formula

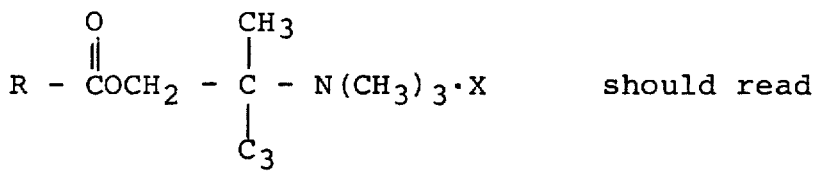   should read

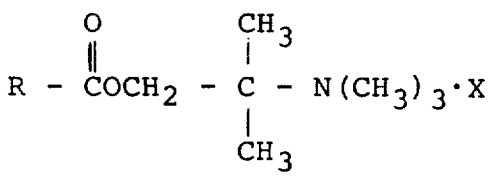

Column 6, lines 12 and 13, "2-dimethylamino-2-methyl-propyl" should read -- 2-dimethylamino-2-methyl-1-propyl --

Column 8, Example 10 in the table, line 33, "oill" should read -- oil --

Signed and Sealed this

Sixth Day of September 1977

[SEAL]

Attest:

RUTH C. MASON
Attesting Officer

LUTRELLE F. PARKER
Acting Commissioner of Patents and Trademarks